(12) United States Patent
Belin et al.

(10) Patent No.: US 7,557,151 B2
(45) Date of Patent: Jul. 7, 2009

(54) RUBBER COMPOSITION COMPRISING AN ITACONIMIDOMALEIMIDE

(75) Inventors: Laure Belin, Riom (FR); Jose Carlos Araujo Da Silva, Pont-du-Chateau (FR); Sylvie Gandon-Pain, Clermont-Ferrand (FR); Geraldine Laffargue, Clermont-Ferrand (FR)

(73) Assignee: Michelin Recherche et Technique S.A., Granges-Paccot (CH)

( * ) Notice: Subject to any disclaimer, the term of this patent is extended or adjusted under 35 U.S.C. 154(b) by 107 days.

(21) Appl. No.: 11/887,050

(22) PCT Filed: Mar. 15, 2006

(86) PCT No.: PCT/EP2006/002391

§ 371 (c)(1),
(2), (4) Date: Sep. 24, 2007

(87) PCT Pub. No.: WO2006/099985

PCT Pub. Date: Sep. 28, 2006

(65) Prior Publication Data

US 2009/0036579 A1 Feb. 5, 2009

(30) Foreign Application Priority Data

Mar. 24, 2005 (FR) .................................. 05 02916

(51) Int. Cl.
*C08K 5/3445* (2006.01)
*C08K 5/16* (2006.01)
*C08K 5/34151* (2006.01)

(52) U.S. Cl. ..................................................... 524/105
(58) Field of Classification Search .................. 524/105
See application file for complete search history.

(56) References Cited

U.S. PATENT DOCUMENTS

| | | | |
|---|---|---|---|
| 4,803,250 A | 2/1989 | Nagasaki et al. | |
| 4,960,833 A | 10/1990 | Nagasaki et al. | |
| 5,328,636 A | 7/1994 | Maly et al. | |
| 5,405,918 A | 4/1995 | Hogt et al. | |
| 5,426,155 A | 6/1995 | Hogt et al. | |
| 5,427,166 A | 6/1995 | Willard, Jr. | |
| 5,503,940 A | 4/1996 | Majumdar et al. | |
| 5,616,279 A | 4/1997 | D'Sidocky et al. | |
| 5,872,188 A | 2/1999 | Datta et al. | |
| 6,079,468 A | 6/2000 | D'Sidocky et al. | |
| 7,442,733 B2 * | 10/2008 | Araujo Da Silva et al. | .. 524/105 |

FOREIGN PATENT DOCUMENTS

| | | |
|---|---|---|
| EP | 0 345 825 | 12/1989 |
| FR | 2 859 730 | 3/2005 |
| WO | WO 92/07904 | 5/1992 |

* cited by examiner

*Primary Examiner*—Ling-Siu Choi
*Assistant Examiner*—Hui Chin
(74) *Attorney, Agent, or Firm*—Buchanan Ingersoll & Rooney PC

(57) ABSTRACT

Rubber composition, which can be used for the manufacture of tires, based on at least one diene elastomer, one reinforcing filler, one vulcanization system and, as antireversion agent, one itaconimidomaleimide compound of formula (R hydrocarbon radical):

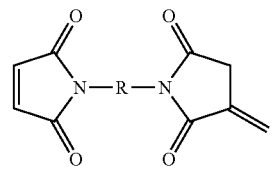

Use of such a composition for the manufacture of a finished article or of a semi-finished product made of rubber intended for a motor vehicle ground-contact system, in particular of a tire.

30 Claims, 2 Drawing Sheets

RUBBER COMPOSITION COMPRISING AN ITACONIMIDOMALEIMIDE

The present invention relates to rubber compositions intended in particular for the manufacture of tyres or tyre semi-finished products and to the antireversion agents which can be used to protect such compositions from heat.

Since the discovery of the vulcanization or crosslinking of rubber by sulphur, numerous improvements have been made to the basic process but sulphur still remains today the essential component from an industrial viewpoint in the crosslinking of diene elastomers.

The principle of vulcanization lies in the creation of sulphur bridges between two macromolecules by reaction with the double bonds of these diene elastomers. One of the noteworthy characteristics of vulcanization is the simplicity with which this reaction can be controlled by addition of compounds exhibiting an accelerating or retarding effect. By varying the respective levels of sulphur and accelerators, it is possible in particular to control the vulcanization efficiency and to obtain sulphur bridges of different configurations which result, for a given rubber composition, in possible adjustments to the properties, both in the raw state and in the cured state.

However, vulcanization of sulphur has the known disadvantage of resulting in limited resistance of the vulcanizates obtained due to the thermal aging of the latter. In particular, the vulcanizates of diene elastomers crosslinked starting from sulphur exhibit high sensitivity to the temperature when the latter reaches a value in the vicinity of the initial curing or vulcanization temperature. This results in a fall in the density of the sulphur bridges initially formed during the vulcanization, the distribution of the vulcanization network changing in the direction of shortening, that is to say a decrease in the polysulphide bridges at the expense of the monosulphide bridges. This phenomenon, known under the term of "reversion", is accompanied by a deterioration in the mechanical properties of the vulcanizate.

Consequently, attempts have been made to eliminate, at the very least limit, this phenomenon of reversion by using, in rubber compositions, specific additives, known as antireversion agents, which make it possible to thermally stabilize the vulcanizates. These antireversion agents currently constitute an important area of research, particularly in the field of tyres, for which optimum thermal stability is desired.

A widely described family of antireversion agents is composed of the maleimide compounds, more particularly of the bismaleimides, used alone or in combination with other compounds (see, for example, EP 191 931 or U.S. Pat. No. 4,803, 250, EP 640 114 or WO93/23467, EP 703 943 or U.S. Pat. No. 5,872,188, EP 709 234 or U.S. Pat. No. 5,503,940, EP 823 453 or U.S. Pat. No. 6,079,468, EP 988 999, U.S. Pat. No. 5,328,636, U.S. Pat. No. 5,616,279, U.S. Pat. No. 5,623,007, WO92/07904 or U.S. Pat. No. 5,426,155, WO95/16738, application JP2001-226528).

The Applicant Companies have discovered, during their research, that, unexpectedly, some highly specific maleimide compounds make it possible to provide the vulcanizates with an improved resistance to reversion in comparison with the abovementioned bismaleimides. In addition, these compounds do not require the presence of any coagent in order to significantly reduce the level of reversion of the vulcanizates.

Consequently, a first subject-matter of the invention is a rubber composition which can be used for the manufacture of tyres based on at least (i) one diene elastomer, (ii) one reinforcing filler, (iii) one vulcanization system and (iv) one maleimide compound, characterized in that the said maleimide compound is an itaconimidomaleimide of specific formula (R hydrocarbon radical):

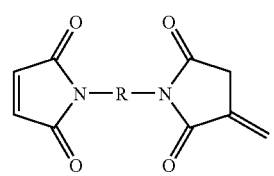

(I)

To the knowledge of the Applicant Companies, such an itaconimidomaleimide compound had never until now been used in a rubber composition which can be used in particular for the manufacture of tyres.

Another subject-matter of the invention is a process for preparing a rubber composition which can be used for the manufacture of tyres and which exhibits an improved resistance to reversion, this composition being based on a diene elastomer, on a reinforcing filler and on a vulcanization system, the said process comprising the following stages:
  incorporating at least one reinforcing filler in a diene elastomer during a first "non-productive" stage, the combined mixture being kneaded thermomechanically, in one or more goes, until a maximum temperature of between 110° C. and 190° C. is reached;
  cooling the combined mixture to a temperature of less than 100° C.;
  subsequently incorporating the vulcanization system during a second "productive" stage;
  kneading the combined mixture up to a maximum temperature of less than 110° C., and being characterized in that an itaconimidomaleimide compound of formula (I) is additionally incorporated during any one of the stages of the process.

Another subject-matter of the invention is the use of a composition according to the invention for the manufacture of a finished article or of a semi-finished product made of rubber intended for any motor vehicle ground-contact system, such as tyre, internal safety support for a tyre, wheel, rubber spring, elastomeric joint, other suspension element and vibration damper.

A very particular subject-matter of the invention is the use of a composition according to the invention for the manufacture of tyres or semi-finished products made of rubber intended for these tyres, these semi-finished products preferably being chosen from the group consisting of treads, crown reinforcing plies, sidewalls, carcass reinforcing plies, beads, protectors, underlayers, rubber blocks and other internal rubbers, in particular decoupling rubbers, intended to provide the bonding or the interface between the abovementioned regions of the tyres.

Another subject-matter of the invention is the finished articles and semi-finished products made of rubber themselves, in particular tyres and semi-finished products for tyres, when they comprise an elastomeric composition in accordance with the invention. The tyres in accordance with the invention are intended in particular for passenger vehicles as for industrial vehicles chosen from vans, heavy-duty vehicles, i.e. underground, bus, heavy road transport vehicles (lorries, tractors, trailers) or offroad vehicles, heavy agricultural vehicles or earthmoving equipment, planes, and other transportation or handling vehicles.

The invention and its advantages will be easily understood in the light of the description and exemplary embodiments which follow as well as of the appended figures, which give a diagrammatic representation of the processes for producing itaconamidomaleimide compounds which can be used in the compositions of the invention.

I. MEASUREMENTS AND TESTS USED

Figure 1:
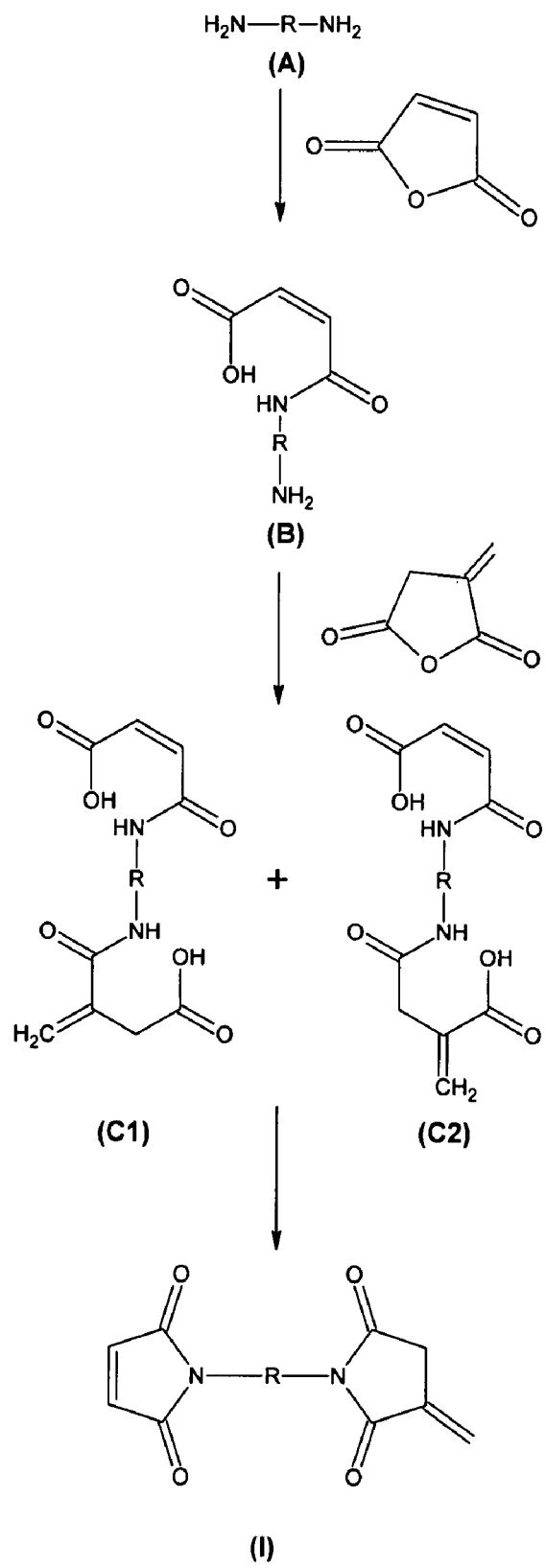
FIG. 1 illustrares a preferred method of synthesizing an itaconamidomaleimide compound.

The rubber compositions are characterized before and after curing, as indicated below.

I-1. Rheometry

The measurements are carried out at 150° C. with an oscillating disc rheometer, according to Standard DIN 53529—part 3 (June 1983). The change in the rheometric torque as a function of time describes the change in the stiffening of the composition as a result of the vulcanization reaction. The measurements are processed according to Standard DIN 53529—part 2 (March 1983): the minimum and maximum torques, measured in dN.m (deciNewton.metre), are respectively referred to as $C_{min}$ and $C_{max}$; the difference, recorded as $\Delta$Torque (in dN.m), between $C_{max}$ and $C_{min}$, which makes it possible to assess the vulcanization yield, is also measured.

Unless otherwise indicated, the mechanical properties indicated below (section I-4) are those measured at "curing optimum", that is to say, in a known way, those obtained, for a specific curing temperature, after the minimum curing time to reach the maximum rheometric torque $C_{max}$.

I-2. Tensile Tests

These tests make it possible to determine the elasticity stresses and the properties at break. Unless otherwise indicated, they are carried out in accordance with French Standard NF T 46-002 of September 1988. The nominal secant moduli (or apparent stresses, in MPa) are measured in second elongation (i.e., after a cycle of accommodation to the degree of extension anticipated for the measurement itself) at 10% elongation (recorded as EM10), 100% elongation (recorded as EM100) and 300% elongation (recorded as EM300). All these tensile measurements are carried out under standard conditions of temperature (23±2° C.) and of humidity (50±5% relative humidity), according to French Standard NF T 40-101 (December 1979).

I-3. Measurement of the Reversion

The reversion can be analysed according to different methods, the aim being to determine, indirectly, the change in the density of the sulphur bridges between a curing "at the optimum" (corresponding to the maximum torque $C_{max}$) and a prolonged curing.

The first approach consists in measuring the change (reduction) in the rheometric torque: the parameter $\Delta R_{60}$ represents the change in % in the torque between $C_{max}$ and the torque measured after curing for 60 min, at a specific curing temperature (for example, 150° C.). The greater the parameter $\Delta R_{60}$, the more significant the reversion phenomenon.

The second approach consists in measuring the change (decrease) in the abovementioned EM100 or EM300 moduli: the parameters $\Delta$EM100 and $\Delta$EM300 correspond to the change in % in the respective moduli measured at the curing optimum ($C_{max}$) and after curing for 6 hours, at a specific curing temperature (150° C.). The greater the parameters $\Delta$EM100 or $\Delta$EM300, the more significant the reversion phenomenon.

II. CONDITIONS FOR IMPLEMENTING THE INVENTION

The rubber compositions according to the invention are based on at least one (that is to say, one or more) diene elastomer(s), one (one or more) reinforcing filler(s), one (one or more) crosslinking system(s) and one (one or more) itaconimidomaleimide compound(s) of abovementioned formula (I).

Of course, the expression composition "based on" should be understood as meaning a composition comprising the reaction mixture and/or product of the various constituents used, some of these base constituents being capable of reacting or intended to react with one another, at least in part, during the various stages of manufacture of the composition, in particular during its vulcanization.

In the present description, unless expressly indicated otherwise, all the percentages (%) indicated are % by weight.

II-1. Diene Elastomer

The term "diene" elastomer or rubber is understood to mean, in a known way, an elastomer resulting at least in part (i.e., homopolymer or a copolymer) from diene monomers (monomers carrying two carbon-carbon double bonds which may or may not be conjugated).

These diene elastomers can be classified into two categories: "essentially unsaturated" or "essentially saturated".

The term "essentially unsaturated" is understood to mean generally a diene elastomer resulting at least in part from conjugated diene monomers having a level of units of diene origin (conjugated dienes) which is greater than 15% (mol %).

Thus it is that, for example, diene elastomers such as butyl rubbers or copolymers of dienes and of α-olefins of EPDM type do not come within the preceding definition and can in particular be described as "essentially saturated" diene elastomers (low or very low level of units of diene origin, always less than 15%).

In the category of "essentially unsaturated" diene elastomers, the term "highly unsaturated" diene elastomer is understood to mean in particular a diene elastomer having a level of units of diene origin (conjugated dienes) which is greater than 50%.

Given these definitions, the term diene elastomer capable of being employed in the compositions in accordance with the invention is understood more particularly to mean:

(a) any homopolymer obtained by polymerization of a conjugated diene monomer having from 4 to 12 carbon atoms;
(b) any copolymer obtained by copolymerization of one or more conjugated dienes with one another or with one or more vinylaromatic compounds having from 8 to 20 carbon atoms;
(c) a ternary copolymer obtained by copolymerization of ethylene and of an α-olefin having 3 to 6 carbon atoms with a non-conjugated diene monomer having from 6 to 12 carbon atoms, such as, for example, the elastomers obtained from ethylene and propylene with a non-conjugated diene monomer of the abovementioned type, such as, in particular, 1,4-hexadiene, ethylidenenorbornene or dicyclopentadiene;
(d) a copolymer of isobutene and of isoprene (butyl rubber) and also the halogenated versions, in particular chlorinated or brominated versions, of this type of copolymer.

Although it applies to any type of diene elastomer, a person skilled in the art of tyres will understand that the present invention is in the first place employed with essentially unsaturated diene elastomers, in particular of the type (a) or (b) above.

The following are suitable in particular as conjugated dienes: 1,3-butadiene, 2-methyl-1,3-butadiene, 2,3-di($C_1$-$C_5$ alkyl)-1,3-butadienes, such as, for example, 2,3-dimethyl-1,3-butadiene, 2,3-diethyl-1,3-butadiene, 2-methyl-3-ethyl-1,3-butadiene or 2-methyl-3-iso-propyl-1,3-butadiene, an aryl-1,3-butadiene, 1,3-pentadiene or 2,4-hexadiene. The following, for example, are suitable as vinylaromatic compounds: styrene, ortho-, meta- or para-methylstyrene, the "vinyltoluene" commercial mixture, para-(tert-butyl)styrene, methoxystyrenes, chlorostyrenes, vinylmesitylene, divinylbenzene or vinylnaphthalene.

The copolymers can comprise between 99% and 20% by weight of diene units and between 1% and 80% by weight of vinylaromatic units. The elastomers can have any microstructure which depends on the polymerization conditions used, in particular on the presence or absence of a modifying and/or randomizing agent and on the amounts of modifying and/or randomizing agent employed. The elastomers can, for example, be block, random, sequential or microsequential elastomers and can be prepared in dispersion or in solution; they can be coupled and/or star-branched or also functionalized with a coupling and/or star-branching or functionalization agent.

The following are suitable: polybutadienes, in particular those having a content of 1,2-units of between 4% and 80% or those having a content of cis-1,4-units of greater than 80%, polyisoprenes, butadiene/styrene copolymers and in particular those having a styrene content of between 5% and 50% by weight and more particularly between 20% and 40%, a content of 1,2-bonds of the butadiene part of between 4% and 65% and a content of trans-1,4-bonds of between 20% and 80%, butadiene/isoprene copolymers, in particular those having an isoprene content of between 5% and 90% by weight and a glass transition temperature (Tg, measured according to ASTM D3418-82) of −40° C. to −80° C., or isoprene/styrene copolymers, in particular those having a styrene content of between 5% and 50% by weight and a Tg of between −25° C. and −50° C. In the case of butadiene/styrene/isoprene copolymers, those having a styrene content of between 5% and 50% by weight and more particularly of between 10% and 40%, an isoprene content of between 15% and 60% by weight and more particularly between 20% and 50%, a butadiene content of between 5% and 50% by weight and more particularly of between 20% and 40%, a content of 1,2-units of the butadiene part of between 4% and 85%, a content of trans-1,4-units of the butadiene part of between 6% and 80%, a content of 1,2-plus 3,4-units of the isoprene part of between 5% and 70% and a content of trans-1,4-units of the isoprene part of between 10% and 50%, and more generally any butadiene/styrene/isoprene copolymer having a Tg of between −20° C. and −70° C., are suitable in particular.

To sum up, the diene elastomer of the composition according to the invention is preferably chosen from the group of the highly unsaturated diene elastomers consisting of polybutadienes (BR), polyisoprenes (IR), natural rubber (NR), butadiene copolymers, isoprene copolymers and the blends of these elastomers. Such copolymers are more preferably chosen from the group consisting of butadiene/styrene copolymers (SBR), isoprene/butadiene copolymers (BIR), isoprene/styrene copolymers (SIR) and isoprene/butadiene/styrene copolymers (SBIR).

According to a particularly preferred embodiment, the diene elastomer is predominantly (that is to say, for more than 50 pce) an SBR, whether an SBR prepared in emulsion ("ESBR") or an SBR prepared in solution ("SSBR"), or an SBR/BR, SBR/NR (or SBR/IR) or also BR/NR (or BR/IR) blend. In the case of an SBR elastomer, use is made in particular of an SBR having a styrene content of between 20% and 30% by weight, a content of vinyl bonds of the butadiene part of between 15% and 65%, a content of trans-1,4-bonds of between 15% and 75% and a Tg of between −20° C. and −55° C.; such an SBR can advantageously be used as a blend with a BR preferably having more than 90% of cis-1,4-bonds.

According to another particularly preferred embodiment, the diene elastomer is predominantly (for more than 50 pce) an isoprene elastomer. This is the case in particular when the compositions of the invention are intended to constitute, in the tyres, rubber matrices of certain treads (for example for industrial vehicles), of crown reinforcing plies (for example of working plies, protection plies or hooping plies), of carcass reinforcing plies, of sidewalls, of beads, of protectors, of underlayers, of rubber blocks and other internal rubbers providing the interface between the abovementioned regions of the tyres.

The compositions according to the invention can, for example, advantageously be used as "decoupling rubbers" in the regions of the tyre ("decoupling regions") having the role of providing mechanical decoupling between two different parts of the said tyre, these regions being, in a known way, exposed to the greatest risks of heating and thus of reversion. They can also advantageously constitute the annular rubber profiled elements used to stiffen the sidewalls of run-flat tyres (see, by way of example, U.S. Pat. No. 5,427,166).

The term "isoprene elastomer" is understood to mean, in a known way, an isoprene homopolymer or copolymer, in other words a diene elastomer chosen from the group consisting of natural rubber (NR), synthetic polyisoprenes (IR), the various copolymers of isoprene and the blends of these elastomers. Mention will in particular be made, among isoprene copolymers, of isobutene/isoprene copolymers (butyl rubber—IIR), isoprene/styrene copolymers (SIR), isoprene/butadiene copolymers (BIR) or isoprene/butadiene/styrene copolymers (SBIR). This isoprene elastomer is preferably natural rubber or a synthetic cis-1,4-polyisoprene; use is preferably made, among these synthetic polyisoprenes, of the polyisoprenes having a level (mol %) of cis-1,4-bonds of greater than 90%, more preferably still of greater than 98%.

According to another preferred embodiment of the invention, in particular when it is intended for a tyre sidewall or for an airtight internal rubber of a tubeless tyre (or other air-impermeable component), the composition in accordance with the invention can comprise at least one essentially saturated diene elastomer, in particular at least one EPDM copolymer or one butyl rubber (optionally chlorinated or brominated), whether these copolymers are used alone or as a blend with highly unsaturated diene elastomers as mentioned above, in particular NR or IR, BR or SBR.

The compositions of the invention can comprise a single diene elastomer or a blend of several diene elastomers, it being possible for the diene elastomer or elastomers to be used in combination with any type of synthetic elastomer other than a diene elastomer, indeed even with polymers other than elastomers, for example thermoplastic polymers.

II-2. Reinforcing Filler

Use may be made of any type of reinforcing filler known for its capabilities of reinforcing a rubber composition which can be used for the manufacture of tyres, for example an organic filler, such as carbon black, or a reinforcing inorganic filler, such as silica, with which, in this second case, a coupling agent will be associated.

All carbon blacks, in particular blacks of the HAF, ISAF or SAF type, conventionally used in tyres ("tyre-grade" blacks) are suitable as carbon blacks. Mention will more particularly be made, among the latter, of the reinforcing carbon blacks of the 100, 200 or 300 series (ASTM grades), such as, for example, the N115, N134, N234, N326, N330, N339, N347 or N375 blacks, or also, depending on the applications targeted, the blacks of higher series (for example, N660, N683 or N772).

The term "reinforcing inorganic filler" should be understood as meaning here, in a known way, any inorganic or mineral filler, whatever its colour and its origin (natural or synthetic), also known as "white" filler, "light" filler or even "non-black" filler, in contrast to carbon black, this inorganic filler being capable of reinforcing, by itself alone, without means other than an intermediate coupling agent, a rubber composition intended for the manufacture of tyres, in other words capable of replacing, in its reinforcing role, a conventional tyre-grade carbon black; such a filler is generally characterized, in a known way, by the presence of hydroxyl (—OH) groups at its surface.

Mineral fillers of the siliceous type, in particular silica ($SiO_2$), or of the aluminous type, in particular alumina ($Al_2O_3$), are suitable in particular as reinforcing inorganic fillers. The silica used can be any reinforcing silica known to a person skilled in the art, in particular any precipitated or pyrogenic silica exhibiting a BET surface and a CTAB specific surface both of less than 450 $m^2$/g, preferably from 30 to 400 $m^2$/g. Mention will be made, as highly dispersible precipitated silicas ("HDS"), for example, of the Ultrasil 7000 and Ultrasil 7005 silicas from Degussa, the Zeosil 1165 MP, 1135 MP and 1115 MP silicas from Rhodia, the Hi-Sil EZ150G silica from PPG or the Zeopol 8715, 8745 and 8755 silicas from Huber.

Mention may be made, as examples of reinforcing aluminas, of the "Baikalox" "A125" or "CR125" aluminas from Baïkowski, the "APA-100RDX" alumina from Condea, the "Aluminoxid C" alumina from Degussa or the "AKP-G015" alumina from Sumitomo Chemicals.

In order to couple the reinforcing inorganic filler to the diene elastomer, use will be made, in a well-known way, of an at least bifunctional coupling agent (or bonding agent) intended to provide a satisfactory connection, of chemical and/or physical nature, between the inorganic filler (surface of its particles) and the diene elastomer, in particular bifunctional organosilanes or polyorganosiloxanes.

Preferably, the level of total reinforcing filler (carbon black and/or reinforcing inorganic filler) is between 20 and 200 pce, more preferably between 30 and 150 pce (parts by weight per hundred parts of elastomer), the optimum being different depending on the applications targeted: the level of reinforcement expected with regard to a bicycle tyre, for example, is in a known way markedly less than that required with regard to a tyre capable of running at high speed in a sustained manner, for example a motorcycle tyre, a tyre for a passenger vehicle or a tyre for a commercial vehicle, such as a heavy-duty vehicle.

II-3. Itaconimidomaleimide

The rubber compositions of the invention have the novel and inventive characteristic of using, as antireversion agent, an itaconimidomaleimide compound comprising both a maleimide functional group and an itaconamide functional group corresponding to the following formula (I):

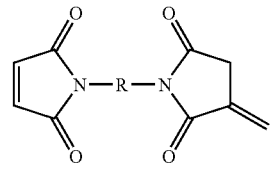

(I)

The radical R is any hydrocarbon radical, aromatic or aliphatic, cyclic or acyclic, substituted or unsubstituted, or linear or branched. Preferably, it comprises from 1 to 25 carbon atoms and optionally one or more heteroatom(s) chosen from O, N and S.

More preferably, R is chosen from the group consisting of alkylenes having from 1 to 20 carbon atoms, cycloalkylenes having from 6 to 24 carbon atoms, arylenes having from 6 to 18 carbon atoms and aralkylenes having from 7 to 25 carbon atoms.

Mention will in particular be made, as examples of itaconimidomaleimides corresponding to this definition, of those belonging to the preferred group consisting of N-(itaconimidoethyl)-maleimide, N-(itaconimidohexamethyl)maleimide, N-(itaconimidododecamethyl)maleimide, N-(itaconimido-1,3-cyclohexyl)maleimide, N-(itaconimido-1,4-cyclohexyl)maleimide, N-(1'-itaconimido-3,3'-dimethyl-4,4'-biphenyl)maleimide, N-(itaconimido-m-phenyl)maleimide, N-(itaconimido-p-phenyl)maleimide, N-(itaconimido-o-phenyl)maleimide, N-(itaconimido-1,3-naphthyl)maleimide, N-(itaconimido-1,4-naphthyl)maleimide, N-(itaconimido-1,5-naphthyl)-maleimide, N-(3-itaconimido-4,6-dimethylphenyl)maleimide, N-(3-itaconimido-4-methylphenyl)maleimide, N-(3-itaconimido-6-methylphenyl)maleimide, N-(3-itaconimido-2-methylphenyl)maleimide, N-(1'-itaconimido-4,4'-methylenebiphenyl)maleimide, N-[2-(methyleneitaconimido)phenyl]methylenemaleimide, N-[3-(methyleneitaconimido)phenyl]-methylenemaleimide, N-[4-(methyleneitaconimido)phenyl]methylenemaleimide, N-(itaconimidooxydipropyl)maleimide, N-(itaconimidooxydi-p-phenyl)maleimide, N-(1'-itaconimido-4,4'-dithiobiphenyl)maleimide, and the mixtures of these compounds.

According to a particularly preferred embodiment of the invention, the itaconamidomaleimide is chosen more preferably from the group consisting of N-(itaconimido-m-phenyl)maleimide, N-(itaconimido-p-phenyl)maleimide, N-(itaconimido-o-phenyl)maleimide, N-(3-itaconimido-4,6-dimethylphenyl)maleimide, N-(3-itaconimido-4-methylphenyl)maleimide, N-(3-itaconimido-6-methylphenyl)maleimide, N-(3-itaconimido-2-methylphenyl)maleimide, N-(1'-itaconimido-4,4'-methylenebiphenyl)maleimide, N-[2-(methyleneitaconimido)phenyl]methylenemaleimide, N-[3-(methyleneitaconimido)phenyl]-methylenemaleimide, N-[4-(methyleneitaconimido)phenyl]methylenemaleimide, and the mixtures of these compounds.

According to a more particularly preferred embodiment, R is a phenylene group, the itaconamidomaleimide selected being more preferably still N-(itaconimido-p-phenyl)-maleimide.

The itaconimidomaleimide is present in the composition according to the invention at a preferred level of between 0.1 and 10 pce. Below the minimum indicated, the technical effect targeted may be inadequate while, above the maximum indicated, the compositions are open to a twofold risk of plasticizing in the raw state and of excessive stiffening in the cured state. For all these reasons, use is made of a level more preferably within a range from 0.2 to 5 pce. An amount within a range from 0.2 to 2.5 pce has proved to be particularly well suited to the tyre application.

The compounds of formula (I) described above can be prepared by a double addition/elimination reaction of a diamine in the presence of maleic anhydride and of itaconic anhydride, followed by a cyclization stage.

By way of example, the appended FIG. 1 illustrates a preferred synthetic route comprising the following stages modelled on known methods (R having the meanings above):

a) the starting material is a diamine (hereinafter product A) of formula (A)

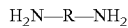

b) it is brought into contact with maleic anhydride in an inert organic solvent, a first addition/elimination reaction takes place to result in a maleamic acid of formula (B), not isolated, which, brought into contact with itaconic anhydride in an inert organic solvent, will bring about a second addition/elimination reaction similar to the preceding one and will result in a maleamic and itaconamic diacid (product C), which can exist in the form of two regioisomers (products C1 and C2) of respective formulae (C1) and (C2):

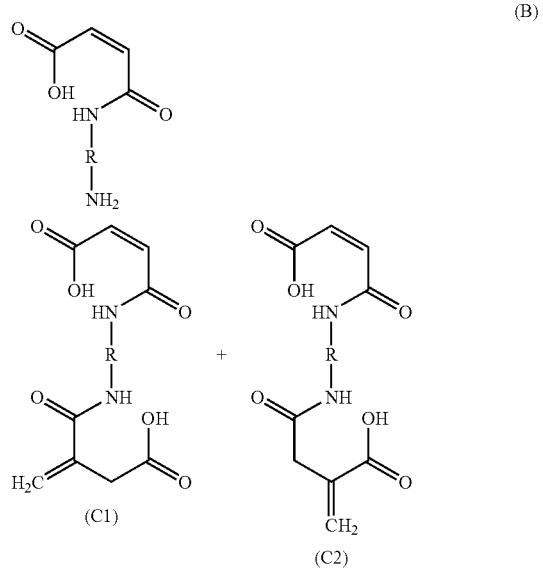

c) then a stage of cyclizing the product C is carried out in the presence of an anhydrous organic solvent (for example, toluene), of a catalyst of the Lewis acid type (for example $ZnCl_2$) and of a cyclizing agent, such as hexamethyldisilazane (HMDS), to generate the targeted product of formula (I):

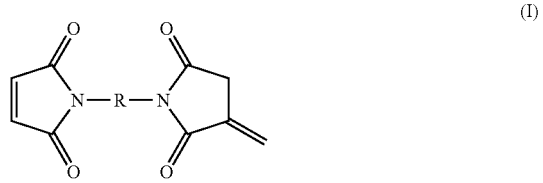

A person skilled in the art will easily understand that a possible alternative form of this synthetic scheme would be to react the diamine in a first step with the itaconic anhydride and then, in a second step, with the maleic anhydride, in other words to reverse the order of the reactants in the above stage b).

II-4. Vulcanization System

The vulcanization system proper is based on sulphur (or on a sulphur-donating agent) and on a primary vulcanization accelerator. Various known secondary accelerators or vulcanization activators, such as zinc oxide, stearic acid or equivalent compounds, or guanidine derivatives (in particular diphenylguanidine), incorporated during the first non-productive phase and/or during the productive phase as described subsequently, are additional to this base vulcanization system.

Sulphur is used at a preferable level of between 0.5 and 10 pce, more preferably of between 1 and 8 pce, in particular between 1 and 6 pce, when the composition of the invention is intended, according to a preferred embodiment of the invention, to constitute a tyre internal rubber, in particular a decoupling rubber.

The primary vulcanization accelerator is, for its part, used at a preferable level of between 0.5 and 10 pce, more preferably of between 0.5 and 5.0 pce.

Such an accelerator, it is known, must allow rubber compositions to crosslink within industrially acceptable times while retaining a minimum safety period ("scorch time") during which the compositions can be shaped without risk of premature vulcanization ("scorch").

Use may be made of any compound capable of acting as vulcanization accelerator for diene elastomers in the presence of sulphur.

Accelerators of the thiazole type and their derivatives of formula (II):

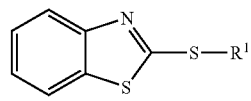

in which $R^1$ represents a hydrogen atom, a 2-mercaptobenzothiazolyl group of formula (III):

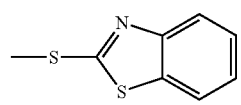

or a group of formula (IV):

in which $R^2$ and $R^3$ independently represent a hydrogen atom, a 2-mercaptobenzothiazolyl group (formula III), a $C_1$-$C_4$ alkyl group or a $C_5$-$C_8$ cycloalkyl group, preferably comprising 6 ring members, it being possible for the said ring to comprise at least one heteroatom, such as S, O or N, are suitable in particular.

Preferred thiazole and derivative accelerators are chosen in particular from the group consisting of 2-mercaptobenzothiazol, 2-mercaptobenzothiazyl disulphide, N-cyclohexyl-2-benzothiazolesulphenamide, N,N-dicyclohexyl-2-benzothiazolesulphenamide, N-tert-butyl-2-benzothiazolesulphenamide, N-cyclohexyl-2-benzothiazolesulphenimide, N-tert-butyl-2-benzothiazolesulphenimide and the mixtures of these compounds.

The compounds of the family of the thiurams (formula V) and the zinc dithiocarbamate derivatives (formula VI):

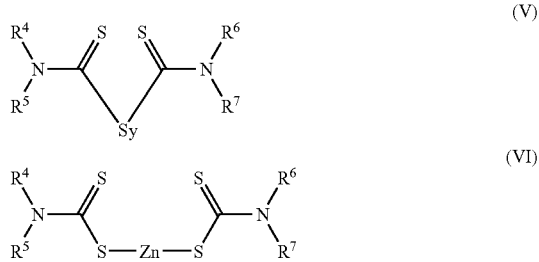

in which y varies from 1 to 4, y being more particularly equal to 1 or 2; and $R^4$, $R^5$, $R^6$ and $R^7$ each independently represent an alkyl group comprising from 1 to 8 carbon atoms, a benzyl group, a combination between $R^4$ and $R^5$ and a combination between $R^6$ and $R^7$ to form a cyclic pentamethylene group or a cyclic methylpentamethylene group in which $R^4$ and $R^5$ and $R^6$ and $R^7$ are connected to one another, are also suitable as accelerators.

Accelerators of thiuram types are chosen in particular from the preferred group consisting of tetramethylthiuram monosulphide, tetramethylthiuram disulphide, tetraethylthiuram disulphide, tetrabutylthiuram disulphide, tetra(isobutyl)thiuram disulphide, tetrabenzyl-thiuram disulphide and the mixtures of these compounds. Tetrabenzylthiuram disulphide is more preferably selected among them.

Mention will be made, as other examples of accelerators which can be used in the compositions of the invention, of zinc dithiocarbamates, in particular zinc tetramethyldithiocarbamate, zinc tetraethyldithiocarbamate and zinc tetrabenzyldithiocarbamate. Among these, zinc tetrabenzyldithiocarbamate is more preferably selected.

To summarize, the primary vulcanization accelerators used in the composition according to the invention are more preferably chosen from the group consisting of 2-mercapto-benzothiazyl disulphide (abbreviated to "MBTS"), N-cyclohexyl-2-benzothiazole-sulphenamide (abbreviated to "CBS"), N,N-dicyclohexyl-2-benzothiazolesulphenamide (abbreviated to "DCBS"), N-tert-butyl-2-benzothiazole-sulphenamide (abbreviated to "TBBS"), N-tert-butyl-2-benzothiazolesulphenimide (abbreviated to "TBSI") and the mixtures of these compounds.

II-5. Various Additives

Of course, the isomeric compositions in accordance with the invention can also comprise all or a portion of the usual additives used in rubber compositions intended for tyre manufacture, such as, for example, plasticizers or extending oils, whether the latter are aromatic or non-aromatic in nature, pigments, protection agents, such as antiozone waxes, chemical antiozonants, antioxidants, antifatigue agents, adhesion promoters, coupling activators, reinforcing resins, methylene acceptors and/or donors, indeed even other antireversion agents, for example conventional bismaleimides.

Preferably, these compositions comprise, as preferred non-aromatic or very slightly aromatic plasticizing agent, at least one compound chosen from the group consisting of naphthenic oils, paraffinic oils, MES oils, TDAE oils, glycerol esters (in particular trioleates), plasticizing hydrocarbon resins preferably exhibiting a high Tg value (preferably of greater than 30° C.), and the mixtures of such compounds.

In the case where the reinforcing filler used is an inorganic filler, use may advantageously be made of agents for covering such an inorganic filler, more generally processing aids capable, in a known way, by virtue of an improvement in the dispersion of the inorganic filler in the rubber matrix and of a lowering in the viscosity of the compositions, of improving their processing property in the raw state.

II-6. Preparation of the Rubber Compositions

The compositions are manufactured in appropriate mixers using two successive preparation phases well known to a person skilled in the art: a first phase of thermomechanical working or kneading ("non-productive" phase) at high temperature, up to a maximum temperature of between 110° C. and 190° C., preferably between 130° C. and 180° C., followed by a second phase of mechanical working ("productive" phase) up to a lower temperature, typically of less than 110° C., for example between 40° C. and 100° C., finishing phase during which the vulcanization system is incorporated.

The process in accordance with the invention for preparing a rubber composition exhibiting an improved resistance to reversion comprises the following stages:

incorporating in a diene elastomer, during a first ("non-productive") stage, at least one reinforcing filler, the combined mixture being kneaded thermomechanically, in one or more goes, until a maximum temperature of between 110° C. and 190° C. is reached;

cooling the combined mixture to a temperature of less than 100° C.;

subsequently incorporating, during a second ("productive") stage, the vulcanization system;

kneading the combined mixture up to a maximum temperature of less than 110° C., and it is characterized in that an itaconimidomaleimide compound of the abovementioned formula (I) is additionally incorporated during any one of the stages of the process:

By way of example, the non-productive phase is carried out in a single thermomechanical stage during which, in a first step, all the necessary base constituents (diene elastomer, reinforcing filler and coupling agent, if necessary, optionally all or a portion of the itaconimidomaleimide compound) are introduced into an appropriate mixer, such as a normal internal mixer, followed, in a second step, for example after kneading for one to two minutes, by the other additives, optional additional covering agents or processing aids, with the exception of the vulcanization system. The total duration of the kneading, in this non-productive phase, is preferably between 1 and 15 min.

After cooling the mixture thus obtained, the vulcanization system and the itaconimidomaleimide compound (all or the remaining portion, if appropriate) are then incorporated in an external mixer, such as an open mill, maintained at low temperature (for example, between 40° C. and 100° C.). The combined mixture is then mixed (productive phase) for a few minutes, for example between 2 and 15 minutes.

The final composition thus obtained can subsequently be calandered, for example in the form of a sheet, or else extruded, for example to form a rubber profiled element used for the manufacture of a tyre semi-finished product, such as plies, bands, underlayers, various rubber blocks, which may or may not be reinforced with textile or metal reinforcing elements, intended to form a part of the structure of the tyre.

The vulcanization (or curing) can subsequently be carried out in a known way at a temperature generally of between 130° C. and 200° C., preferably under pressure, for a sufficient time which can vary, for example, between 5 and 90 min depending in particular on the curing temperature, the vulcanization system adopted and the vulcanization kinetics of the composition under consideration.

The invention relates to the rubber compositions described above both in the "raw" state (i.e., before curing) and in the "cured" or vulcanized state (i.e., after vulcanization).

III. EXAMPLES OF THE IMPLEMENTATION OF THE INVENTION

III-1. Synthesis of Itaconimidomaleimide

N-(p-Itaconimidophenyl)maleimide is prepared by reaction of 1,4-phenylenediamine with maleic anhydride and then itaconic anhydride; the diacid then generated is subsequently cyclized, the model being a process for the synthesis of N-alkyl- and N-arylimide derivatives as described in *J. Org. Chem.*, Vol. 62, No. 8, 2652-2654, 1997.

Figure 2:
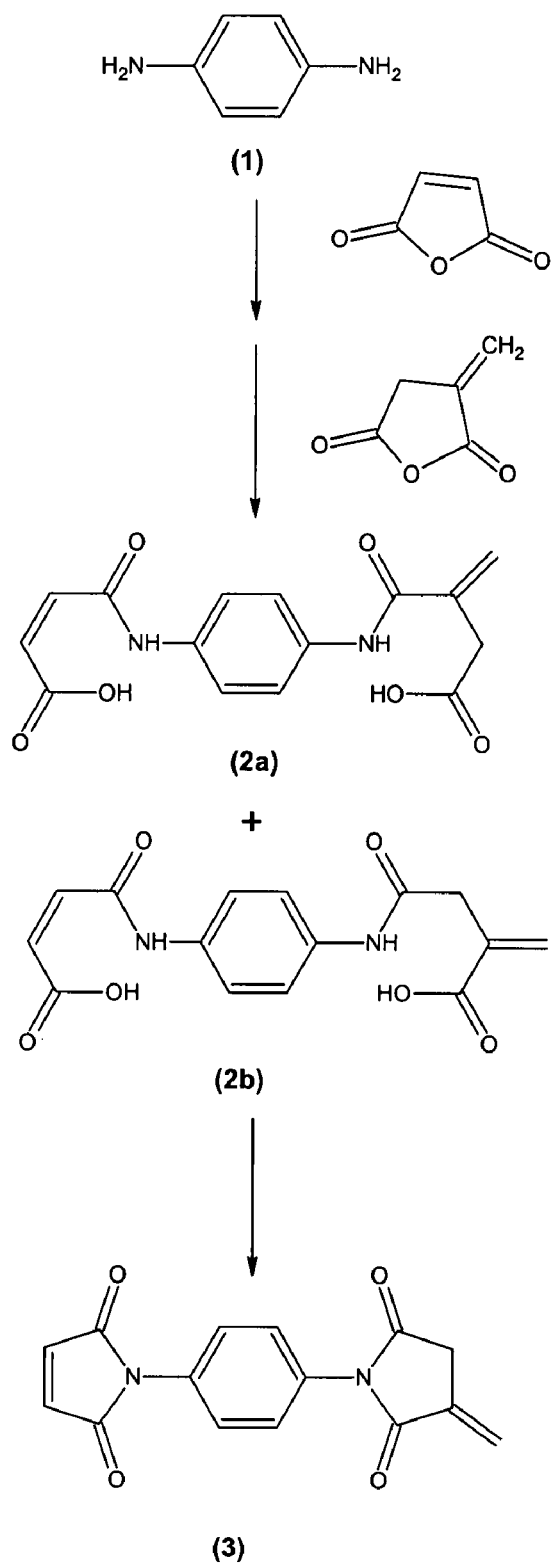
FIG. 2 illustrates a method of synthesizing N-(p-itaconimidopheny)maleimide.

More specifically, this synthesis is carried out in two stages as represented diagrammatically in the appended FIG. 2.

A) $1^{st}$ Stage: Synthesis of 1,4-phenylene-N-itaconamic-N'-maleamic diacid (Products (2a) and (2b) in FIG. 2)

1,4-Phenylenediamine (1) (10.50 g, i.e. 0.094 mol, 1 equivalent) and 222 ml of THF (tetrahydrofuran) are added to a 500 ml two-necked flask. A solution of maleic anhydride (9.34 g, i.e. 0.094 mol, 1 eq.) in 48 ml of THF is added to this solution in 10 minutes at ambient temperature under an argon atmosphere. After stirring at ambient temperature for 1 h 30, a solution of itaconic anhydride (16.68 ml, i.e. 0.141 mol, 1.5 eq.) in 60 ml of THF is added in 10 minutes to the medium, which has become heterogeneous and orange in colour. The medium is left stirring at ambient temperature for 16 hours. The precipitate is filtered off on a sintered glass funnel and then rinsed with ethyl ether. It is dried at ambient temperature; 30 g of 1,4-phenylene-N-itaconamic-N'-maleamic diacid are thus obtained in the form of a fine light-yellow powder.

B) $2^{nd}$ Stage: Synthesis of N-(p-itaconimidophenyl)maleimide (Product (3) in FIG. 2)

The diacid (2a and 2b) (11.7 g, i.e. 0.0347 mol, 1 eq.) and 1.5 ml of anhydrous toluene are introduced into a dry three-necked flask under inert atmosphere. The mixture formed is subjected to mechanical stirring for a few minutes at ambient temperature and then $ZnCl_2$ (10.16 g, i.e. 0.728 mol, 2.1 eq.) is added all at once. The reaction mixture is brought to 80° C. and then HMDS (18.16 ml, i.e. 0.0869 mol, 2.5 eq.) is added in 10 minutes. The mixture is left for 24 hours with vigorous stirring and heating and then it is evaporated to dryness using a rotary evaporator (water bath at 80° C. under 1 mmHg). The crude product obtained is taken up in 745 ml of dichloromethane at 50° C. for 20 min in order to dissolve as much as possible of product and filtration is carried out under hot conditions on a sintered glass funnel, the beige precipitate collected corresponding to the $ZnCl_2$. The organic phase isolated is then washed with respectively 100 ml of a saturated $NaHCO_3$ solution and then a saturated $Na_2CO_3$ solution, dried over $MgSO_4$, filtered and evaporated.

1.70 g of N-(p-itaconimidophenyl)maleimide (3) are thus obtained in the form of a highly pulverulent beige powder.

III-2. Preparation of the Compositions

The following tests are carried out in the following way: the diene elastomer (or the blend of diene elastomers, if appropriate) and the reinforcing filler (carbon black) are introduced into a conventional internal paddle mixer of the "Banbury" type (capacity: approximately 3.5 litres), filled to 70% and having an initial vessel temperature of approximately 60° C., and then, after kneading for 1 to 2 minutes, the various other ingredients are introduced, with the exception of the vulcanization system and the antireversion agent.

Thermomechanical working (non-productive phase) is then carried out in one stage (total duration of the kneading equal to approximately 5 min) until a maximum "dropping" temperature of approximately 160° C. is reached. The mixture thus obtained is recovered and cooled and then the vulcanization system and (if it is present in the composition) the antireversion agent are added on an external mixer (homofinisher) at 40° C., the combined mixture being mixed (productive phase) on this open mill for 3 to 4 minutes.

The compositions thus obtained are subsequently calendered in the form of sheets (thickness of 2 to 3 mm) or of fine sheets of rubber, for the measurement of their physical or mechanical properties, or extruded to form profiled elements which can be used directly, after cutting and/or assembling to the desired dimensions, as tyre semi-finished product.

III-3. Characterization Tests

Results

The aim of this test is to demonstrate the improved resistance to reversion of a composition according to the invention intended to constitute a decoupling rubber situated between the crown reinforcement and the radial carcass reinforcement of a tyre of the earthmoving equipment type.

This composition according to the invention is compared with two control compositions comprising or not comprising an antireversion agent, the three compositions tested being identical apart from the following differences:
- composition T-1: control without antireversion agent;
- composition T-2: control with conventional antireversion agent (bismaleimide);
- composition C-1: composition according to the invention (itaconimidomaleimide).

The bismaleimide compound used in the control composition T-2 is meta-phenylene-bismaleimide (abbreviated to "MPBM"), which is well known to a person skilled in the art and which corresponds to the following specific formula:

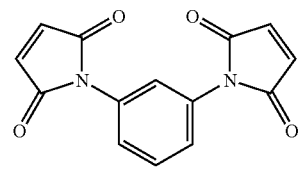

It should be remembered that the itaconimidomaleimide used in the composition according to the invention C-1 corresponds to the following specific formula:

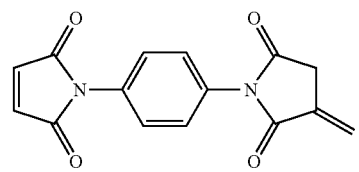

Thus, the essential characteristic distinguishing the two above compounds, and thus the composition according to the invention C-1 from the control composition T-2, is the presence on one and just one of the two cyclic imide groups of the double bond in the exo position.

The two maleimide compounds are used at an isomolar level.

Tables 1 and 2 give the formulations of the various compositions (Table 1—levels of the various products, expressed in pce), the properties after curing, the rheometric properties and various parameters by which the reversion is measured. The resistance to reversion of the compositions is assessed by monitoring the change in the rheometric torque after 60 min at 150° C. The thermal stability of the compositions is also assessed by the change in the nominal secant modulus at 100% elongation and at 300% elongation, between the measurement at the curing optimum and after prolonged curing for 6 hours (temperature of 150° C.).

On reading Table 2, it is noted first of all that the standard properties of the compositions after curing are substantially identical: tensile moduli (EM100, EM300) and EM300/EM100 ratio (known index of reinforcement) very similar, rheometric properties fairly similar.

However, it is the parameters for measuring the reversion which demonstrate all the advantage of the composition according to the invention with respect to the two control compositions.

The thermal stability of the composition C-1 turns out to be notable, markedly greater than observed with regard to the two controls T-1 and T-2, whatever the parameter used (in accordance with the indications given in section I-5): the loss $\Delta R_{60}$, like the changes in moduli $\Delta EM100$ and $\Delta EM300$, all very clearly indicate that the phenomenon of reversion does not occur with regard to the composition of the invention, whereas it remains relatively pronounced with regard to the control composition T-2, despite the presence of conventional bismaleimide (MPBM).

Thus, the presence of the double bond in the exo position on the itaconamide ring on one of the imide groups of the molecule confers this unexpected thermal stability on the rubber compositions of the invention.

TABLE 1

| Composition No.: | T-1 | T-2 | C-1 |
|---|---|---|---|
| NR (1) | 100 | 100 | 100 |
| Carbon black (2) | 35 | 35 | 35 |
| ZnO (3) | 5 | 5 | 5 |
| Stearic acid (4) | 1.5 | 1.5 | 1.5 |
| Antioxidant (5) | 1.5 | 1.5 | 1.5 |
| Bismaleimide (6) | — | 1.5 | — |
| Itaconimidomaleimide (7) | — | — | 1.6 |
| Sulphur (8) | 1.6 | 1.6 | 1.6 |
| Accelerator (9) | 0.6 | 0.6 | 0.6 |

(1) natural rubber (peptized);
(2) N375 (Cabot);
(3) zinc oxide (industrial grade, Umicore);
(4) stearin ("Pristerene 4931") from Uniqema;
(5) N-(1,3-dimethylbutyl-N-phenyl-para-phenylenediamine ("Santoflex 13" from Flexsys);
(6) MPBM (Safic Alcan);
(7) N-(p-maleimidophenyl)itaconimide, synthesized according to section III-1;
(8) sulphur (synthetic sulphur from Solvay);
(9) TBBS (N-tert-butyl-2-benzothiazolesulphenamide) ("Santocure TBBS" from Flexsys).

TABLE 2

| Composition | T1 | T2 | C1 |
|---|---|---|---|
| Rheometric properties at 150° C.: | | | |
| $C_{min}$ (dN·m) | 0.5 | 0.5 | 0.5 |
| $C_{max}$ (dN·m) | 6.1 | 9.3 | 8.0 |
| $\Delta$Torque (dN·m) | 5.6 | 8.7 | 7.4 |
| Properties after cooling at the optimum at 150° C.: | | | |
| EM100 (MPa) | 1.48 | 1.71 | 1.53 |
| EM300 (MPa) | 1.84 | 2.27 | 1.94 |
| EM300/EM100 | 1.24 | 1.32 | 1.26 |

TABLE 2-continued

| Composition | T1 | T2 | C1 |
|---|---|---|---|
| Reversion (1 hour at 150° C.): | | | |
| $\Delta R60$ (%) € | −14 | −10 | −5 |
| Properties after prolonged curing for 6 hours at 150° C. and reversion: | | | |
| EM100 (MPa) | 1.12 | 1.42 | 1.58 |
| EM300 (MPa) | 1.25 | 1.70 | 1.96 |
| $\Delta$EM100 (%) | −24 | −17 | 3 |
| $\Delta$EM300 (%) | −32 | −25 | 1 |

The invention claimed is:

1. A rubber composition which can be used for the manufacture of tires based on at least (i) one diene elastomer, (ii) one reinforcing filler, (iii) one vulcanization system and (iv) one maleimide compound, wherein said maleimide compound is an itaconimidomaleimide of formula (I), wherein R represents radical consisting of carbon, hydrogen and optionally one or more heteroatoms selected from the group consisting of O, N and S:

2. The composition according to claim 1, R comprising from 1 to 25 carbon atoms and optionally one or more heteroatom(s) selected from the group consisting of O, N and S.

3. The composition according to claim 2, R being selected from the group consisting of alkylenes having from 1 to 20 carbon atoms, cycloalkylenes having from 6 to 24 carbon atoms, arylenes having from 6 to 18 carbon atoms and aralkylenes having from 7 to 25 carbon atoms.

4. The composition according to claim 3, the itaconimidomaleimide being selected from the group consisting of N-(itaconimido-m-phenyl) maleimide, N-(itaconimido-p-phenyl)maleimide, N-(itaconimido-o-phenyl) maleimide, N-(3-itaconimido-4,6-dimethylphenyl)maleimide, N-(3-itaconimido-4-methylphenyl)maleimide, N-(3-itaconimido-6-methylphenyl)maleimide, N-(3-itaconimido-2-methylphenyl)maleimide, N-(1'-itaconimido-4,4'-methylenebiphenyl) maleimide, N-[2-(methyleneitaconimido)phenyl] methylenemaleimide, N-[3-(methyleneitaconimido)phenyl] methylenemaleimide, N-[4-(methylene-itaconimido)phenyl] methylenemaleimide, and mixtures of these compounds.

5. The composition according to claim 3, R being a phenylene group.

6. The composition according to claim 5, the itaconimidomaleimide being N-(p-itaconimidophenyl)maleimide.

7. The composition according to claim 1, the diene elastomer being selected from the group consisting of polybutadienes, natural rubber, synthetic polyisoprenes, butadiene copolymers, isoprene copolymers and blends of these elastomers.

8. The composition according to claim 1, the reinforcing filler being present at a level of between 20 and 200 pce (parts by weight per hundred of diene elastomer).

9. The composition according to claim 1, the reinforcing filler being predominantly an inorganic filler.

10. The composition according to claim 1, the reinforcing filler being predominantly an organic filler.

11. The composition according to claim 7, the diene elastomer being an isoprene elastomer, or a natural rubber.

12. The composition according to claim 1, the level of itaconimidomaleimide being between 0.1 and 10 pce.

13. The composition according to claim 12, the level of itaconimidomaleimide being within a range from 0.2 to 2.5 pce.

14. The composition according to claim 1 further comprising a primary vulcanization accelerator selected from the group consisting of 2-mercaptobenzothiazyl disulphide, N-cyclohexyl-2-benzothiazolesulphenamide, N,N-dicyclohexyl-2-benzothiazolesulphenamide, N-tert-butyl-2-benzothiazolesulphenamide, N-tert-butyl -2-benzothiazolesulphenimide and mixtures of these compounds.

15. The composition according to claim 8, the reinforcing filler being present at a level of between 30 and 150 pce.

16. The composition according to claim 9, wherein the inorganic filler comprises silica.

17. The composition according to claim 10, wherein the organic filler comprises carbon black.

18. The composition according to claim 11, wherein the isoprene elastomers comprises a synthetic polyisoprene.

19. A process for preparing a rubber composition which can be used for the manufacture of tires and which exhibits an improved resistance to reversion, this composition being based on a diene elastomer, on a reinforcing filler and on a vulcanization system, said process comprising the following stages:
   incorporating at least one reinforcing filler in a diene elastomer during a first stage, the combined mixture being kneaded thermomechanically, in one or more goes, until a maximum temperature of between 110° C. and 190° C. is reached;
   cooling the combined mixture to a temperature of less than 100° C.;
   subsequently incorporating the vulcanization system during a second stage; and
   kneading the combined mixture up to a maximum temperature of less than 110° C., wherein an itaconimidomaleimide compound of formula (I)

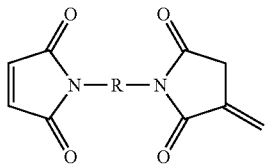

is additionally incorporated during any one of the stages of the process, wherein R represents radical consisting of carbon, hydrogen and optionally one or more heteroatoms selected from the group consisting of O, N and S.

20. The process according to claim 19, R comprising from 1 to 25 carbon atoms.

21. The process according to claim 20, R being selected from the group consisting of alkylenes having from 1 to 20 carbon atoms, cycloalkylenes having from 6 to 24 carbon atoms, arylenes having from 6 to 18 carbon atoms and aralkylenes having from 7 to 25 carbon atoms.

22. The process according to claim 21, the itaconimidomaleimide being selected from the group consisting of N-(itaconimido-m-phenyl) maleimide, N-(itaconimido-p-phenyl) maleimide, N-(itaconimido-o-phenyl)maleimide, N-(3-itaconimido-4,6-dimethylphenyl)maleimide, N-(3-itaconimido-4-methylphenyl)maleimide, N-(3-itaconimido-6-methylphenyl)maleimide, N-(3-itaconimido-2-methylphenyl)maleimide, N-(1'-itaconimido-4,4'-methylenebiphenyl)maleimide, N-[2-(methyleneitaconimido)phenyl]methylenemaleimide, N-[3-(methyleneitaconimido)phenyl]methylenemaleimide, N-[4-(methylene-itaconimido)phenyl]methylenemaleimide, and mixtures of these compounds.

23. The process according to claim 21, R being a phenylene group.

24. The process according to claim 23, the itaconimidomaleimide being N-(p-itaconimidophenyl)maleimide.

25. The process according to claim 19, the diene elastomer being selected from the group consisting of polybutadienes, natural rubber, synthetic polyisoprenes, butadiene copolymers, isoprene copolymers and blends of these elastomers.

26. The process according to claim 19, the reinforcing filler being present at a level of between 20 and 200 pce (parts by weight per hundred of diene elastomer).

27. The process according to claim 25, the level of itaconimidomaleimide being between 0.1 and 10 pce.

28. The process according to claim 27, the level of itaconimidomaleimide being within a range from 0.2 to 2.5 pce.

29. The process according to claim 26, the reinforcing filler being present at a level of between 30 and 150 pce.

30. A finished article or semi-finished product intended for a motor vehicle ground-contact system comprising the composition according to claim 1.

* * * * *